US006210676B1

(12) United States Patent
Callister et al.

(10) Patent No.: US 6,210,676 B1
(45) Date of Patent: Apr. 3, 2001

(54) **COMPOSITIONS AND METHODS USING THE BORRELIACIDAL EPITOPE(S) OF *BORRELIA BURGDORFERI* OUTER SURFACE PROTEIN C (OSPC) FOR THE DIAGNOSIS AND PREVENTION OF LYME DISEASE**

(75) Inventors: Steven M. Callister; Steven D. Lovrich, both of La Crosse; Ronald F. Schell, Dade; Dean A. Jobe, La Crosse, all of WI (US)

(73) Assignee: Gundersen Lutheran Medical Foundation, La Crosse, WI (US)

( * ) Notice: Subject to any disclaimer, the term of this patent is extended or adjusted under 35 U.S.C. 154(b) by 0 days.

(21) Appl. No.: 09/364,083

(22) Filed: Jul. 30, 1999

Related U.S. Application Data

(60) Provisional application No. 60/094,955, filed on Jul. 31, 1998, now abandoned.

(51) Int. Cl.⁷ .......................... A61K 39/02; A61K 45/00; A61K 39/00; A61K 38/00; C07K 1/00
(52) U.S. Cl. .................................. 424/190.1; 424/234.1; 424/282.1; 424/184.1; 424/828; 530/300; 530/324; 530/350; 530/825; 435/7.1; 435/975
(58) Field of Search .............................. 424/190.1, 192.1, 424/184.1, 234.1, 282.1, 828; 514/2; 530/300, 324, 350, 825, 820; 435/975, 7.1

(56) References Cited

U.S. PATENT DOCUMENTS

| | | |
|---|---|---|
| 5,385,826 | 1/1995 | Schell et al. ........................ 435/7.32 |
| 5,656,451 | 8/1997 | Flavell et al. ........................ 435/69.1 |
| 5,773,232 | 6/1998 | Wier ..................................... 435/7.24 |
| 5,777,095 | 7/1998 | Barbour et al. ..................... 536/23.7 |
| 5,807,685 | 9/1998 | Flavell et al. ......................... 435/7.1 |
| 5,846,946 | 12/1998 | Huebner et al. ....................... 514/44 |
| 5,853,987 | 12/1998 | Guo et al. ................................. 435/6 |
| 5,854,395 | 12/1998 | Champion et al. .................. 530/350 |
| 5,856,447 | 1/1999 | Simon et al. ...................... 530/388.4 |
| 5,912,117 | 6/1999 | Dodge et al. ............................ 435/6 |

FOREIGN PATENT DOCUMENTS

| | | |
|---|---|---|
| 2084413 | 12/1991 | (CA). |
| WO 94/25596 | 11/1994 | (WO). |
| WO 95/11998 * | 5/1995 | (WO). |
| WO 97/42221 | 11/1997 | (WO). |

OTHER PUBLICATIONS

Yu. Dissertation Abstracts International, vol. 57–02B, abstract, 1996.*
Centers for Disease Control and Prevention. Lyme Disease—United States, 1996. Morbid Mortal Weekly Report 46: 531–535.
Centers for Disease Control and Prevention. Lyme Disease—United States, 1995. Morbid Mortal Weekly Report 45: 481–484.

Aguero–Rosenfeld, M.E. et al., Evolution of the Serologic Response to *Borrelia burgdorferi* in Treated Patients with Culture–Confirmed Erythema Migrans. *Journal of Clinical Microbiology.* 1996:34:1–9.
Agger, W. et al., Lyme Disease: Clinical Features, Classification, and Epidemiology in the Upper Midwest. *Medicine.* 1991:70:83–90.
Appel, M.J.G. et al., Experimental Lyme Disease in Dogs Produces Arthritis and Persistent Infection. *The Journal of Infectious Disease.* 1993:167:651–664.
Bakken, L.L. et al., Interlaboratory Comparison of Test Results for Detection of Lyme Disease by 516 Participants in the Wisconsin State Laboratory of Hygiene/College of American Pathologists Proficiency Testing Program. *Journal of Clinical Microbiology.* 1997:35:537–543.
Barthold, S.W. et al., Protective and Arthritis–Resolving Activity in Sera of Mice Infected with *Borrelia burgdorferi*. *Clinical Infectious Diseases.* 1997:25:S9–S17.
Bockenstedt, L.K. et al., *Borrelia burgdorferi* Strain–Specific Osp C–Mediated Immunity in Mice. *Infection & Immunity.* 1997:65:4661–4667.
Callister, S.M. et al., Characterization of the Borreliacidal Antibody Response to *Borrelia burgdorferi* in Humans: A Serodiagnostic Test. *The Journal of Infectious Diseases.* 1993:167:158–164.
Callister, S.M. et al., Lyme Disease Assay Which Detects Killed *Borrelia burgdorferi*. *Journal of Clinical Microbiology.* 1991:29:1773–1776.
Callister, S.M. et al., Detection of Borreliacidal Antibodies by Flow Cytometry. *Archives of Internal Medicine.* 1994:154:1625–1632.
Callister, S.M. et al., Sensitivity and Specificity of the Borreliacidal–Antibody Test During Early Lyme Disease: a "Gold Standard"? *Clinical & Diagnostic Laboratory Immunology.* 1996:3:399–402.
Callister, S.M. et al., Laboratory Serodiagnosis of Lyme Borreliosis. *Journal of Spirochetal Tick–Borne Disease.* 1998:5:4–10.
Cox, D.L et al., Limited Surface Exposure of *Borrelia burgdorferi* Outer Surface Lipoproteins. *Proc. Natl. Acad. Sci. USA.* 1996:93:7973–7978.
Creson, J.R. et al., Detection of Anti–*Borrelia burgdorferi* Antibody Responses with the Borreliacidal Antibody Test, Indirect Fluorescent–Antibody Assay Performed by Flow Cytometry, and Western Immunoblotting. *Clinical & Diagnostic Laboratory Immunology.* 1996:3:184–190.

(List continued on next page.)

Primary Examiner—Lynette R. F. Smith
Assistant Examiner—S. Devi
(74) Attorney, Agent, or Firm—DeWitt Ross & Stevens SC

(57) ABSTRACT

An OspC Dra fragment fusion peptide isolated from *Borrelia burgdorferi* is described herein for the prevention, treatment and early diagnosis of Lyme disease in humans and other animals. This invention also relates to a screening method detecting anti-Osp borreliacidal antibody activity, and antibodies reacting with a protein fragment encoded by a DraI-SmaI DNA fragment of OspC.

11 Claims, 4 Drawing Sheets

OTHER PUBLICATIONS

Fikrig, E. et al., Roles of OspA, OspB, and Flagellin in Protective Immunity to Lyme Borreliosis in Laboratory Mice. *Infection & Immunity.* 1992:60:657–661.

Fikrig, E. et al., Sera from Patients with Chronic Lyme Disease Protect Mice from Lyme Borreliosis. *The Journal of Infectious Diseases.* 1994:169:568–574.

Fukunaga, M. et al., Outer Surface Protein C Gene Sequence Analysis of *Borrelia burgdorferi* Sensu Lato Isolates from Japan. *Journal of Clinical Microbiology.* 1995:33:2415–2420.

Fung, B.P. et al., Humoral Immune Response to Outer Surface Protein C of *Borrelia burgdorferi* and in Lyme Disease: Role of the Immunoglobulin M Response in the Serodiagnosis of Early Infection. *Infection & Immunity.* 1994:62:3213–3221.

Gerber, M.A. et al., Recombinant Outer Surface Protein C ELISA for the Diagnosis of Early Lyme Disease. *The Journal of Infectious Diseases.* 1995:171:724–727.

Gilmore, Jr., R.D. et al., Outer Surface Protein C (OspC), but not P39, is a Protective Immunogen Against a Tick–Transmitted *Borrelia burgdorferi* Challenge: Evidence for a Conformational Protective Epitope in OspC. *Infection & Immunity.* 1996:64:2234–2239.

Jauris–Heipke, S. et al., Molecular Analysis of Genes Encoding Outer Surface Protein C (OspC) of *Borrelia burgdorferi* Sensu Lato: Relationship to ospA Genotype and Evidence of Lateral Gene Exchange of ospC. *Journal of Clinical Microbiology.* 1995:33:1860–1866.

Johnson, R.C. et al., Passive Immunization of Hamsters Against Experimental Infection with the Lyme Disease Spirochete. *Infection & Immunity.* 1986:53:713–714.

Johnson, B.J.B. et al., Incomplete Protection of Hamsters Vaccinated with Unlipidated OspA from *Borrelia burgdorferi* Infection is Associated with Low Levels of Antibody to an Epitope Defined by mAb LA–2. *Vaccine.* 1995:13:1086–1094.

Kochi, S.K. et al., Role of Immunoglobulin G in Killing of *Borrelia burgdorferi* by the Classical Complement Pathway. *Infection & Immunity.* 1988:56:314–321.

Kurtti, T.J. et al., Resistance to Tick–Borne Spirochete Challenge Induced by *Borrelia burgdorferi* Strains that Differ in Expression of Outer Surface Proteins. *Infection & Immunity.* 1996:64:4148–4153.

Lech, K. et al., Media Preparation and Bacterological Tools. *Current Protocols in Molecular Biology.* (John Wiley & Sons) 1997:1.1.1–1.1.6.

Livey, I. et al., Evidence for Lateral Transfer and Recombination in OspC Variation in Lyme Disease Borrelia. *Molecular Microbiology.* 1995:18:257–269.

Lovrich, S.D. et al., Seroprotective Groups Among Isolates of *Borrelia burgdorferi. Infection & Immunity.* 1993:61:4367–4374.

Lovrich, S.D. et al., Seroprotective Groups of Lyme Borreliosis Spirochetes from North America and Europe. *The Journal of Infectious Diseases.* 1994:170:115.121.

Lovrich, S.D. et al., Abilities of OspA Proteins from Different Seroprotective Groups of *Borrelia burgdorferi* to Protect Hamsters from Infection. *Infection & Immunity.* 1995:63:2113–2119.

Ma, J. et al., Molecular Analysis of Neutralizing Epitopes on Outer Surface Proteins A and B of *Borrelia burgdorferi. Infection & Immunity.* 1995:63:2221–2227.

Magnarelli, L.A. et al., Use of Recombinant Antigens of *Borrelia burgdorferi* in Serologic Tests for Diagnosis of Lyme Borreliosis. *Journal of Clinical Microbiology.* 1996:34:237–240.

Magnarelli, L.A. et al., Serologic Diagnosis of Canine and Equine Borreliosis: Use of Recombinant Antigens in Enzyme–Linked Immunosorbent Assays. *Journal of Clinical Microbiology.* 1997:35:169–173.

McCaulley, M.E. et al., The Costs of Lyme Disease. *Arch. Intern. Med.* 1997:157:817–818.

Nelson, R.A. et al., Immobilization of Treponema Pallidum In Vitro by Antibody Produced in Syphilitic Infection. *J. Exp. Med.* 1949:29:369–393.

Pachner, A.R. et al., The Triad of Neurological Manifestations of Lyme Disease. *Neurology.* 1985:35:47–53.

Padilla, M.L., et al., Characterization of the Protective Borreliacidal Antibody Response in Humans and Hamsters After Vaccination with a *Borrelia burgdorferi* Outer Surface Protein A Vaccine. *The Journal of Infectious Diseases.* 1996:74:736–746.

Padula, S.J. et al., Molecular Characterization and Expression of p23 (OspC) from a North American Strain of *Borrelia burgdorferi. Infection & Immunity.* 1993:61:5097–5105.

Padula, S.J. et al., Use of Recombinant OspC from *Borrelia burgdorferi* for Serodiagnosis of Early Lyme Disease. *Journal of Clinical Microbiology.* 1994:32:1733–1738.

Pavia, C.S. et al., Antiborrelial Activity of Serum from Rats Injected with the Lyme Disease Spirochete. *The Journal of Infectious Diseases.* 1991:163:656–659.

Pavia, C.S. et al., Assessment of In Vitro Growth of *Borrelia burgdorferi* by Tritiated Adenien Incorporation. (New York Medical College–Department of Medicine, Microbiology & Immunology). pp. 410–413.

Piesman, J. et al., Duration of Immunity to Reinfection with Tick–Transmitted *Borrelia burgdorferi* in Naturally Infected Mice. *Infection & Immunity.* 1997:65:4043–4047.

Probert, W.S. et al., Protection of C3H/HeN Mice from Challenge with *Borrelia burgdorferi* Through Active Immunization with OspA, OspB, or OspC, but not with OspD or the 83–Kioldalton Antigen. *Infection & Immunity.* 1994:62:1920–1926.

Probert, W.S. et al., Immunization with Outer Surface Protein (Osp)A, but not OspC, Provides Cross–Protection of Mice Challenged with North American Isolates of *Borrelia burgdorferi. The Journal of Infectious Diseases.* 1997:175:400–405.

Rauer, S. et al., Enzyme–Linked Immunosorbent Assay Using Recombinant OspC and the Internal 14–kDa Flagellin Fragment for Serodiagnosis of Early Lyme Disease. *Journal of Clinical Microbiology.* 1998:36:857–861.

Rousselle, J.C. et al., Borreliacidal Antibody Production Against Outer Surface Protein C of *Borrelia burgdorferi. The Journal of Infectious Disease.* 1998:178:001–009.

Sadziene, A. et al., In Vitro Inhibition of *Borrelia burgdorferi* Growth by Antibodies. *The Journal of Infectious Diseases.* 1993:167:165–172.

Sadziene, A. et al., A Bactericidal Antibody to *Borrelia burgdorferi* is Directed Against a Variable Region of the OspB Protein. *Infection & Immunity.* 1994:62:2037–2045.

Sambri, V. et al., Animal and Human Antibodies Reactive with the Outer Surface Protein A and B of *Borrelia burgdorferi* are Borreliacidal, In Vitro, in the Presence of Complement. *FEMS Immunology & Medical Microbiology.* 1993:7:67–72.

Schell, R.F. et al., The Borreliacidal Antibody Test: An Alternative Approach for Confirming Lyme Borreliosis. *Journal of Spirochetal and Tick–Borne Diseases.* 1997:4:4–6.

Schmitz, J.L. et al., Passive Immunization Prevents Induction of Lyme Arthritis in LSH Hamsters. *Infection & Immunity.* 1990:58:144–148.

Schmitz, J.L. et al., Characterization of the Protective Antibody Response to *Borrelia burgdorferi* in Experimentally Infected LSH Hamsters. *Infection & Immunity.* 1991:59:1916–1921.

Schutzer, S.E. et al., Detection of Lyme Disease After OspA Vaccine. *The New England Journal of Medicine.* 1997:337:794–795.

Schwan, T.G. et al., Induction of an Outer Surface Protein on *Borrelia burgdorferi* During Tick Feeding. *Proc. Natl. Acad. Sci. USA.* 1995:92:2909–2913.

Sigal, L.H., The Lyme Disease Controversy. *Arch. Intern. Med.* 1996:156:1493–1500.

Smith, D.B. et al., Expression and Purification of Glutathione–S–Transferase Fusion Proteins. *Current Protocols in Molecular Biology.* (John Wiley & Sons) 1994:16.7.1–16.7.7.

SmithKline Beecham, SmithKline Beecham's LYMErix™ Found Safe and Effective for Prevention of Lyme Disease by FDA Advisory Committee. Press Release dated May 26, 1998.

Steere A.C. et al., The Early Clinical Manifestations of Lyme Disease. *Annals of Internal Medicine.* 1983:99:76–82.

Steere, A.C. et al., Lyme Carditis: Cardiac Abnormalities of Lyme Disease. *Annals of Internal Medicine.* 1980:93:8–16.

Stevenson, B. et al., Expression and Sequence of Outer Surface Protein C Among North American Isolates of *Borrelia burgdorferi*. *FEMS Microbiology Letters.* 1994:124:367–372.

Stevenson, B. et al., Temperature–Related Differential Expression of Antigens in the Lyme Disease Spirochete, *Borrelia burgdorferi*. *Infection & Immunity.* 1995:63:4535–4539.

Straubinger, R.K. et al., Sera from OspA–Vaccinated Dogs, but not Those from Tick–Infected Dogs, Inhibit In Vitro Growth of *Borrelia Burgdorferi*. *Journal of Clinical Microbiology.* 1995:33:2745–2751.

Strickland, G.T. et al., Utilization and Cost of Serologic Tests for Lyme Disease in Maryland. *The Journal of Infectious Diseases.* 1997:176:819–821.

Theisen, M. et al., Evolution of the *Borrelia burgdorferi* Outer Surface Protein OspC. *Journal of Bacteriology.* 1995:177:3036–3044.

Wilske, B. et al., Phenotypic Analysis of Outer Surface Protein C (OspC) of *Borrelia burgdorferi* Sensu Lato by Monoclonal Antibodies: Relationship to Genospecies and OspA Serotype. *Journal of Clinical Microbiology.* 1995:33:103–109.

Zhang, Y.Q. et al., *Borrelia burgdorferi* Enzyme–Linked Immunosorbent Assay for Discrimination of OspA Vaccination from Spirochete Infection. *Journal of Clinical Microbiology.* 1997:35:233–238.

Zhong, W. et al., Resolution of Experimental and Tick–Borne *Borrelia burgdorferi* in Mice by Passibe, but not Active Immunization Using Recombinant OspC. *Eur. J. Immunology.* 1999:29:946–957.

Zhong, W. et al., Therapeutic Passive Vaccination Against Chronic Lyme Disease in Mice. *Proc. Natl. Acad. Sci. USA.* 1997:94:12533–12539.

* cited by examiner

*B. burgdorferi* isolate S-1-10 *ospC* gene

*B. burgdorferi* isolate S-1-10 *ospC* gene- Dra fragment

FIG. 3

```
         10        20        30        40        50
ATGAAACTGAAGGTAACAGTCAACGGCACTGCGTATGACGTTGACGTTGA
 M  K  L  K  V  T  V  N  G  T  A  Y  D  V  D  V  D>

60        70        80        90       100
CGTCGACAAGTCACACGAAAACCCGATGGGCACCATCCTGTTCGGCGGCG
 V  D  K  S  H  E  N  P  M  G  T  I  L  F  G  G>

110       120       130       140       150
GCACCGGCGGCGCGCCGGCACCGGCAGCAGGTGGCGCAGGCGCCGGTAAG
 G  T  G  G  A  P  A  P  A  A  G  G  A  G  A  G  K>

160       170       180       190       200
GCCGGAGAGGGCGAGATTCCCGCTCCGCTGGCCGGCACCGTCTCCAAGAT
 A  G  E  G  E  I  P  A  P  L  A  G  T  V  S  K  I>

210       220       230       240       250
CCTCGTGAAGGAGGGTGACACGGTCAAGGCTGGTCAGACCGTGCTCGTTC
 L  V  K  E  G  D  T  V  K  A  G  Q  T  V  L  V>

260       270       280       290       300
TCGAGGCCATGAAGATGGAGACCGAGATCAACGCTCCCACCGACGGCAAG
 L  E  A  M  K  M  E  T  E  I  N  A  P  T  D  G  K>

310       320       330       340       350
GTCGAGAAGGTCCTGGTCAAGGAGCGTGACGCGGTGCAGGGCGGTCAGGG
 V  E  K  V  L  V  K  E  R  D  A  V  Q  G  G  Q  G>

360       370       380       390       400
TCTCATCAAGATCGGGGATCTCGAGCTCATCGAAGGTCGCGAAAGCTTCA
 L  I  K  I  G  D  L  E  L  I  E  G  R  E  S  F>

410       420       430       440       450
GCTGGGATCCGGTACCGATATCAGATCTCCC AAAACACATAATACTAAA
 S  W  D  P  V  P  I  S  D  L  P  K  T  H  N  T  K>

460       470       480       490       500
GACAAGGGTGCTGAAGAACTTGTAAAGTTAGCTGAATCAGTAGCAGGCTT
 D  K  G  A  E  E  L  V  K  L  A  E  S  V  A  G  L>

510       520       530       540       550
GCTAAAAGTAGCGCAAGAAACACTAAATAATTCAGTTAAAGAACTTACAA
 L  K  V  A  Q  E  T  L  N  N  S  V  K  E  L  T>

560       570       580       590       600
GTCCTGTTGTGGCAGAAAGTCCAAAAAAACCTTAACCCGGGGCGGCCGCG
 S  P  V  V  A  E  S  P  K  K  P  *
```

FIG. 4

SEQUENCE LISTING

```
<160> NUMBER OF SEQ ID NOS: 4

<210> SEQ ID NO 1
<211> LENGTH: 600
<212> TYPE: DNA
<213> ORGANISM: Borrelia burgdorferi
<220> FEATURE:
<221> NAME/KEY: misc_feature
<222> LOCATION: (433)..(582)
<223> OTHER INFORMATION: DNA sequence unique to OspC Dra fragment of B.
      burgdorferi S-1-10.
<220> FEATURE:
<221> NAME/KEY: CDS
<222> LOCATION: (1)..(582)

<400> SEQUENCE: 1 atg aaa ctg aag gta aca gtc aac ggc act gcg tat gac gtt gac gtt       48
Met Lys Leu Lys Val Thr Val Asn Gly Thr Ala Tyr Asp Val Asp Val
```

```
        1               5                  10                 15
gac gtc gac aag tca cac gaa aac ccg atg ggc acc atc ctg ttc ggc      96
Asp Val Asp Lys Ser His Glu Asn Pro Met Gly Thr Ile Leu Phe Gly
                20                 25                 30 ggc ggc acc ggc ggc gcg ccg gca ccg gca gca ggt ggc gca ggc gcc     144
Gly Gly Thr Gly Gly Ala Pro Ala Pro Ala Ala Gly Gly Ala Gly Ala
        35                 40                 45 ggt aag gcc gga gag ggc gag att ccc gct ccg ctg gcc ggc acc gtc     192
Gly Lys Ala Gly Glu Gly Glu Ile Pro Ala Pro Leu Ala Gly Thr Val
    50                 55                 60 tcc aag atc ctc gtg aag gag ggt gac acg gtc aag gct ggt cag acc     240
Ser Lys Ile Leu Val Lys Glu Gly Asp Thr Val Lys Ala Gly Gln Thr
65                 70                 75                 80 gtg ctc gtt ctc gag gcc atg aag atg gag acc gag atc aac gct ccc     288
Val Leu Val Leu Glu Ala Met Lys Met Glu Thr Glu Ile Asn Ala Pro
                85                 90                 95 acc gac ggc aag gtc gag aag gtc ctg gtc aag gag cgt gac gcg gtg     336
Thr Asp Gly Lys Val Glu Lys Val Leu Val Lys Glu Arg Asp Ala Val
                100                105                110 cag ggc ggt cag ggt ctc atc aag atc ggg gat ctc gag ctc atc gaa     384
Gln Gly Gly Gln Gly Leu Ile Lys Ile Gly Asp Leu Glu Leu Ile Glu
        115                120                125 ggt cgc gaa agc ttc agc tgg gat ccg gta ccg ata tca gat ctc cca     432
Gly Arg Glu Ser Phe Ser Trp Asp Pro Val Pro Ile Ser Asp Leu Pro
    130                135                140 aaa aca cat aat act aaa gac aag ggt gct gaa gaa ctt gta aag tta     480
Lys Thr His Asn Thr Lys Asp Lys Gly Ala Glu Glu Leu Val Lys Leu
145                150                155                160 gct gaa tca gta gca ggc ttg cta aaa gta gcg caa gaa aca cta aat     528
Ala Glu Ser Val Ala Gly Leu Leu Lys Val Ala Gln Glu Thr Leu Asn
                165                170                175 aat tca gtt aaa gaa ctt aca agt cct gtt gtg gca gaa agt cca aaa     576
Asn Ser Val Lys Glu Leu Thr Ser Pro Val Val Ala Glu Ser Pro Lys
                180                185                190 aaa cct taacccgggg cggccgcg                                          600
Lys Pro
```

<210> SEQ ID NO 2
<211> LENGTH: 194
<212> TYPE: PRT
<213> ORGANISM: Borrelia burgdorferi

<400> SEQUENCE: 2

```
Met Lys Leu Lys Val Thr Val Asn Gly Thr Ala Tyr Asp Val Asp Val
 1               5                  10                 15

Asp Val Asp Lys Ser His Glu Asn Pro Met Gly Thr Ile Leu Phe Gly
                20                 25                 30

Gly Gly Thr Gly Gly Ala Pro Ala Pro Ala Ala Gly Gly Ala Gly Ala
        35                 40                 45

Gly Lys Ala Gly Glu Gly Glu Ile Pro Ala Pro Leu Ala Gly Thr Val
    50                 55                 60

Ser Lys Ile Leu Val Lys Glu Gly Asp Thr Val Lys Ala Gly Gln Thr
65                 70                 75                 80

Val Leu Val Leu Glu Ala Met Lys Met Glu Thr Glu Ile Asn Ala Pro
                85                 90                 95

Thr Asp Gly Lys Val Glu Lys Val Leu Val Lys Glu Arg Asp Ala Val
                100                105                110

Gln Gly Gly Gln Gly Leu Ile Lys Ile Gly Asp Leu Glu Leu Ile Glu
```

-continued

```
                    115                 120                 125
Gly Arg Glu Ser Phe Ser Trp Asp Pro Val Pro Ile Ser Asp Leu Pro
    130                 135                 140

Lys Thr His Asn Thr Lys Asp Lys Gly Ala Glu Glu Leu Val Lys Leu
145                 150                 155                 160

Ala Glu Ser Val Ala Gly Leu Leu Lys Val Ala Gln Glu Thr Leu Asn
                165                 170                 175

Asn Ser Val Lys Glu Leu Thr Ser Pro Val Val Ala Glu Ser Pro Lys
                180                 185                 190

Lys Pro

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 3
cgtggatcca tgaaaaagaa tacattaagt gcgata                              36

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 4
aattcccggg ttaaggtttt tttggactttt cgtc                               34
```

COMPOSITIONS AND METHODS USING THE BORRELIACIDAL EPITOPE(S) OF *BORRELIA BURGDORFERI* OUTER SURFACE PROTEIN C (OSPC) FOR THE DIAGNOSIS AND PREVENTION OF LYME DISEASE

This application claims priority to provisional application Ser. No. 60/094,955, filed Jul. 31, 1998, now abandoned.

BIBLIOGRAPHY

Complete bibliographic citations of the references referred to herein by number in parentheses can be found in the Bibliography section, immediately preceding the claims.

FIELD OF THE INVENTION

This invention relates to compositions and methods useful for the prevention, treatment and early diagnosis of Lyme disease in humans and other animals. More particularly, this invention relates to outer surface protein (Osp) polypeptides which are able to elicit in a patient the formation of a specific immune response which is effective to diagnose, predict successful eradication of infection or protect against Lyme disease in a mammalian host. This invention also relates to a screening method to detect anti-Osp borreliacidal antibody activity, and antibodies which react with a protein fragment encoded by a DraI-SmaI DNA fragment of OspC. Also within the scope of this invention are antibodies directed against Osp polypeptides, diagnostic kits comprising the antibodies or the polypeptides, and vaccines using borreliacidal epitopes of OspA, OspB or OspC or a conserved DNA sequence fragment together with or without a vaccine carrier.

DESCRIPTION OF THE PRIOR ART

Lyme disease (*Lyme borreliosis*) is spread by a bite from an infected tick, and is the most commonly reported tick-borne infection in Europe and North America (1). This multi-system disorder has caused significant morbidity worldwide.

Lyme disease is caused by the spirochete *Borrelia burgdorferi* (*B.b.*), which is primarily transmitted during the blood feeding of *Ixodes ssp* ticks. Initially, spirochetes infect the skin and, in the majority of early cases, cause an erythema migrans lesion (2). Those stricken may not become ill for weeks, and nervous system symptoms (headaches, dizziness, hearing problems, tingling and trouble concentrating) may not occur for weeks or months. It is now known that infection can spread to the nervous system or joints, and the risk of neurological or joint complications increases the longer the disease goes untreated. Infection can be asymptomatic, or have a range of clinical presentations, depending on the tissues affected, the duration of infection, host factors such as the vulnerability of the immune system and immunogenetic factors which could predispose a patient to the development of certain complications.

The treatment of symptomatic patients is currently with a range of antibiotics, e.g., tetracyclines, penicillin and cephalosporins, but studies show mixed results. Left untreated, the bacteria can spread to the central nervous system, heart, brain, or joints, causing arthritis, cardiac infections and neurologic problems, and in rare cases, death (3–6).

Upon infection with borrelia, B cells in the body begin producing antibodies which recognize the foreign organism. There are at least two functional types of antibodies produced in response to a borrelia infection. One response is a nonspecific binding/opsonizing (coating) response which "marks" the antigen and may result in ingestion of *B.b.* by phagocytic cells. These non-specific antibodies are produced against proteins common among several bacterial species (viz. 41 kDa proteins to many bacterial flagella). Thus, these antibodies will recognize and attach to similar antigens on other bacteria. Because of this, diagnostic tests which detect these non-specific binding/opsonizing antibodies are generally nonspecific.

A second functional antibody response is the production of borreliacidal (lethal) antibodies which specifically recognize epitopes on some individual proteins of the *B.b.* organisms. After attachment of these antibodies to the *B.b.* organisms, complement interacts with the antibodies to form a membrane attack complex which kills the *B.b.* organism without the necessity of scavenging by phagocytic cells. This highly specific borreliacidal antibody response is often detectable within the first 2 weeks of infection. The successful detection and induction of borreliacidal antibodies is gaining importance in the Lyme disease diagnostic and prevention armamentarium.

Shortly after the discovery of *Lyme borreliosis*, researchers determined that vaccination of experimental animals with whole *B.b.* provided protection against challenge (7,8). Additional studies established the role of antibody-mediated protection and confirmed the ability of vaccination with *B.b.* to induce antibodies which provide protection against *B.b.* infection (9–11). To date, vaccination of animals with Osps of *B.b.*, especially OspA (12–14), OspB (12,14), and OspC (14–16), have provided protection against infection with the Lyme spirochete. Protection after vaccination with OspA and OspB have been shown to be due to the induction of borreliacidal antibodies which specifically killed the *B.b.* organisms (13,14,17–24). In contrast, anti-OspC borreliacidal antibodies have not been detected after vaccination (14–16) and investigators have postulated that protection after vaccination with OspC is due to other mechanisms (16).

Most of the efforts to date have focused on developing an OspA vaccine primarily because of the large amounts of OspA expressed on the surface of many *B.b.* laboratory isolates. To date, most borrelia spirochetes have had outer surfaces comprised mainly of OspA. Therefore, it has been believed that inducing borreliacidal antibodies against OspA would provide protection against the spirochetes. Smith-Kline Beecham (Philadelphia, Pa.) and Pasteur Merieux Connaught (Lyon, France) have developed vaccines based on the generation of borreliacidal antibodies to OspA. The SmithKline Beecham vaccine has been approved for general use, and the Pasteur Merieux Connaught vaccine is currently being assessed by the U.S. Food and Drug Administration. As one would expect, OspA vaccines have been shown to be effective in animal models when the animals have been needle challenged. In addition, OspA vaccination has provided protection against ticks infected with *B.b.* However, protection against a tick challenge has been dependent on the presence of high levels of anti-OspA borreliacidal antibodies. Schwan et al. (28) recently demonstrated that spirochetes in infected ticks downregulate OspA on their surface during ingestion of a blood meal. Thus, OspA vaccines must induce high titers of anti-OspA borreliacidal antibodies to destroy the spirochetes in the midgut of infected ticks before they downregulate OspA. Therefore, the duration of high titers of anti-OspA borreliacidal antibodies is a critical determinant of the long-term efficacy of an OspA vaccine.

The applicants recently demonstrated the inability of a commercial OspA vaccination to sustain adequate levels of anti-OspA borreliacidal antibodies in humans (23). It is also unlikely that an anamnestic response will occur quickly enough to eliminate B.b. organisms from infected ticks. In support, infection with B.b. has been documented in OspA-vaccinated humans and dogs (26,27). These results highlight the need to evaluate other *Lyme borreliosis* vaccine components.

In addition, Lyme disease is ordinarily diagnosed by detecting antibodies in the blood or cerebral spinal fluid, but the most commonly used tests are often inaccurate. False-negative, and more commonly, false-positive results continue to plague the serodiagnosis of Lyme disease. Several schemes using conventional diagnostic assays have been developed to more accurately detect Lyme disease. Unfortunately, little improvement has occurred and misdiagnosis continues to cause significant economic and health effects. In addition, the recent approval of an OspA Lyme disease vaccine will further confound conventional diagnostic testing. Thus, a sensitive and specific Lyme disease test which can be made widely available as a commercial kit and can discriminate between vaccinated individuals and patients with Lyme disease is still needed.

Detection of borreliacidal antibodies may also solve this problem. Borreliacidal antibodies have been shown to serve as the basis for a sensitive and highly specific serodiagnostic test (17,25–27). In fact, a diagnostic assay for Lyme disease, which detects this antibody response, has been previously developed, patented (37), and is commercially available. This test relies on detection of highly specific borreliacidal antibodies which are induced by several B.b. Osps shortly after infection. It is important to note if sufficiently high levels of borreliacidal antibodies are induced by vaccination, the vaccinee is protected. However, if an individual is infected before borreliacidal antibodies are present, the person can get Lyme disease despite the eventual presence of high concentrations of borreliacidal antibodies. This test provides a more sensitive and specific alternative approach for confirming Lyme disease. In addition, antibody detected by the borreliacidal antibody test does not correlate with antibody detected by conventional assays. In hamster studies, detection of borreliacidal antibodies decreased with elimination of B.b. from the host (43). In contrast, the antibody responses detected by conventional assays remain elevated or continues to expand. These results suggest that the borreliacidal antibody test is a prognostic indicator for clearance of the spirochete.

Callister et al. (30) recently showed the ability to increase the sensitivity of the borreliacidal antibody test while maintaining the exquisite specificity through the use of a test antigen (B.b. 50772) which does not contain OspA or OspB on the surface. The increased sensitivity with B.b. 50772 is proposed by the applicants to be due to detection of borreliacidal antibodies against OspC or other Osps. These results greatly increase the utility of the borreliacidal antibody testing procedure disclosed in U.S. Pat. No. 5,385,826 to Schell et al., which is incorporated herein in its entirety.

In addition, several investigators have demonstrated the ability of vaccination with OspC to protect laboratory animals against needle challenge (14–15) and natural infection (16). A recent investigation also showed that passive transfer of immune sera to OspC could resolve arthritis, carditis and infection with B.b. (44). These results demonstrate that vaccination with OspC may be more effective than vaccinations with OspA. However, since high concentrations of anti-OspC borreliacidal antibodies have not been detected in immune serum (14–16), there has been speculation that additional mechanisms are responsible for OspC-mediated protection (16). Not knowing the mechanism makes it much more difficult to pursue an OspC Lyme disease vaccine. In addition, the pursuit of OspC as a *Lyme borreliosis* vaccine candidate has been hindered because OspC appears to be more immunologically and genetically heterogeneous than OspA (35–37), causing researchers to speculate that development of a comprehensive OspC vaccine is economically unfeasible. However, Schwan et al. (28) recently showed that relatively large amounts of OspC are rapidly synthesized by B.b. shortly after attachment of infected ticks to mammalian hosts and that OspA is no longer expressed in high concentration on the surface of B.b.

It has recently been reported that B.b. organisms upregulate OspC and concomitantly downregulate OspA shortly before tick inoculation of the host with the spirochete (31,32). This explains why anti-OspC antibodies are among the first antibody responses detected in patients with early *Lyme borreliosis*. In response, several investigators have attempted or are attempting to develop enzyme-linked immunosorbent assays (ELISA) using whole recombinant OspC proteins (38–42). These diagnostic assays have been reasonably sensitive but have continued to lack specificity. In addition, the anti-OspC antibody responses detected by these assays may remain elevated or continue to expand even after clearance of B.b. from the host. Of particular concern is the propensity of OspC to cross-react with antibodies in sera from patients with other illnesses such as cytomegalovirus (CMV) or Epstein-Barr virus (EBV) and give a false-positive reaction. Because of this significant lack of specificity and the lack of prognostic potential, OspC ELISAs remain significantly less than ideal.

SUMMARY OF THE INVENTION

The present invention is directed to an isolated, immunogenic polypeptide fragment of OspC of *Borrelia burgdorferi* consisting essentially of an epitope of OspC having an amino acid sequence as shown in residues 145 to 194 of SEQ. ID. NO: 2.

The present invention is also directed to an isolated polypeptide having an amino acid sequence as shown in residues 145 to 194 of SEQ. ID. NO: 2.

The present invention is also directed to an isolated DNA molecule encoding a polypeptide having an amino acid sequence as shown in residues 145 to 194 of SEQ. ID. NO: 2.

The present invention is also directed to an expression vector comprising an isolated DNA encoding a polypeptide having an amino acid sequence as shown in residues 145 to 194 of SEQ. ID. NO: 2.

Further, the present invention is directed to a pharmaceutical composition to vaccinate against and to treat borrelia infection in mammals, including humans, the composition comprising an amount of an isolated polypeptide consisting essentially of an amino acid sequence as shown in residues 145 to 194 of SEQ. ID. NO: 2, the amount being effective to prevent or to treat borrelia infection in mammals.

The present invention is also directed to a method to prevent and to treat borrelia infection in mammals, including humans, comprising administering to a patient in need thereof an amount of an isolated polypeptide consisting essentially of an amino acid sequence as shown in residues 145 to 194 of SEQ. ID. NO: 2, the amount being effective to prevent or to treat borrelia infection in the patient.

The present invention is also directed to a kit for diagnosing borrelia infection in mammals, including humans, the kit comprising an isolated polypeptide having an amino acid sequence as shown in residues 145 to 194 of SEQ. ID. NO: 2, disposed in a suitable container therefor, and instructions for use of the kit.

The present invention is also directed to a method to detect borrelia infection in mammals, including humans, comprising contacting a body fluid of a mammalian host suspected to suffer from borrelia infection with an isolated polypeptide having an amino acid sequence as shown in residues 145 to 194 of SEQ. ID. NO: 2; and then determining whether the isolated polypeptide is conjugated to antibodies present in the body fluid of the mammalian host, whereby presence of conjugation indicates presence of borrelia infection in the host.

Advantageously, the polypeptide of this invention is not confounded by previous vaccinations against Lyme disease. Detection of anti-OspC borreliacidal antibodies against the Dra fragment is useful for diagnosing Lyme disease in patients from anywhere in the world and also for vaccination against Lyme disease caused by Borrelia ssp. There are 3 major species of Lyme disease spirochetes now known: *B.b.*, *B. garinii* and *B. afzelii*. The inventors have detected anti-OspC borreliacidal antibodies in patients from Slovenia infected with *B. afzelii*. They detected these anti-OspC borreliacidal antibodies by using *B.b.* 50772, the same isolate used to detect a response in patients infected with *B.b.* Thus, the Dra fragment of OspC appears to be conserved in all species of borrelia.

A Dra fragment-based ELISA is an excellent complementary test to the borreliacidal antibody test. Most importantly, a Dra fragment-based ELISA is easily manufactured as a commercial kit and discriminates between patients vaccinated with early Lyme disease.

A test which detects borreliacidal antibodies against the borreliacidal epitope(s) of OspA and OspB in addition to OspC would give reduced cross-reactivity, increased specificity, greater accuracy, and fewer false-positive diagnoses. Detection of anti-OspC borreliacidal antibodies advantageously gives an early diagnosis which anti-OspA and anti-OspB borreliacidal antibodies cannot do. However, the identification of the borreliacidal epitope(s) of OspB and OspA are also valuable additions to a diagnostic test.

Inclusion of borreliacidal epitopes of OspA and OspB with the Dra fragment of OspC also yields a more comprehensive *Lyme borreliosis* vaccine.

Further objects and advantages of the invention will appear more fully from the following detailed description of the preferred embodiment of the invention made in conjunction with the accompanying tables and drawings.

BRIEF DESCRIPTION OF THE DRAWINGS

Figure 1:
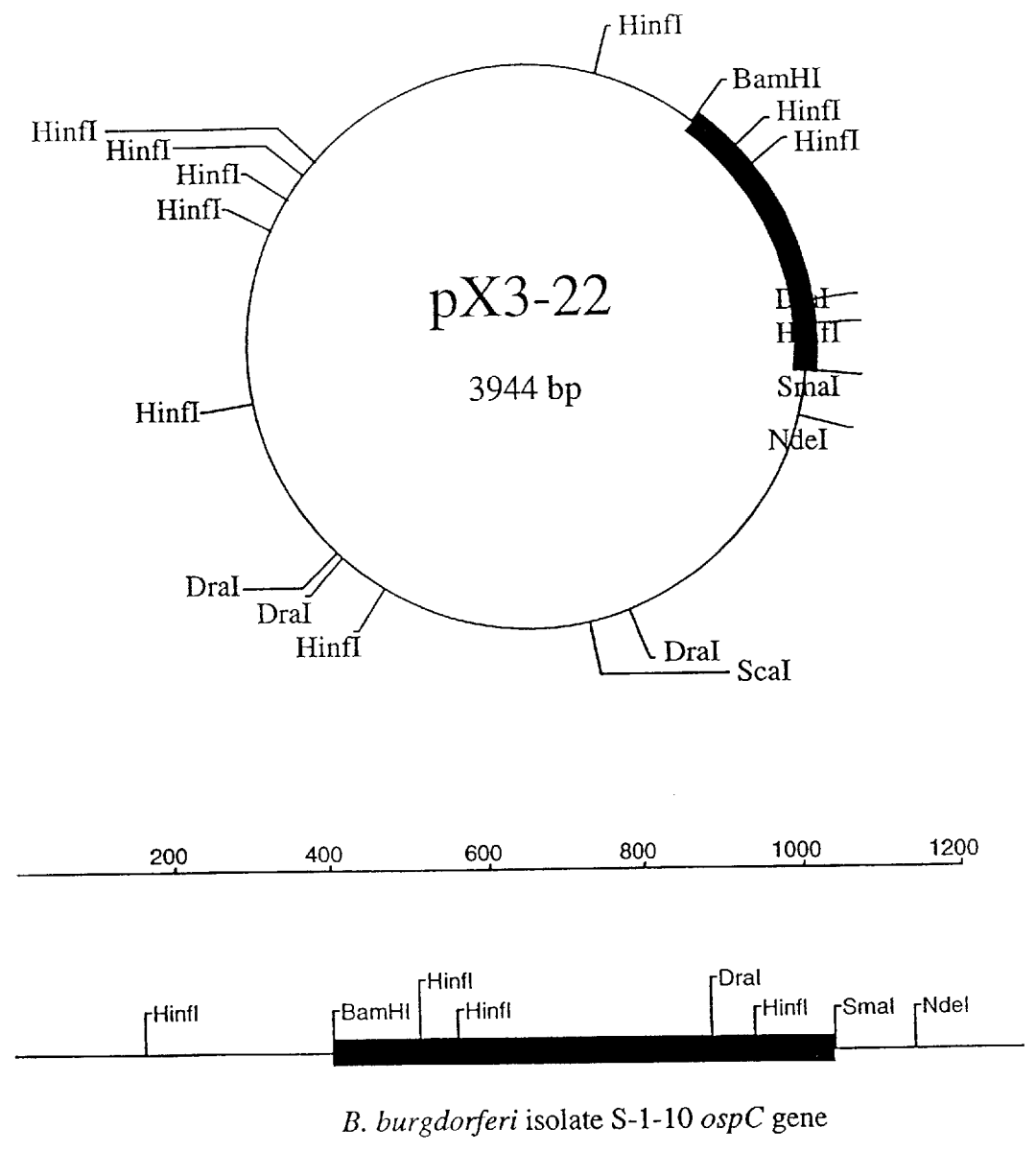

FIG. 1 is a restriction Map of Plasmid pX3-22. The shaded box represents the area containing the *B.b.* S-1-10 ospC gene.

Figure 2:
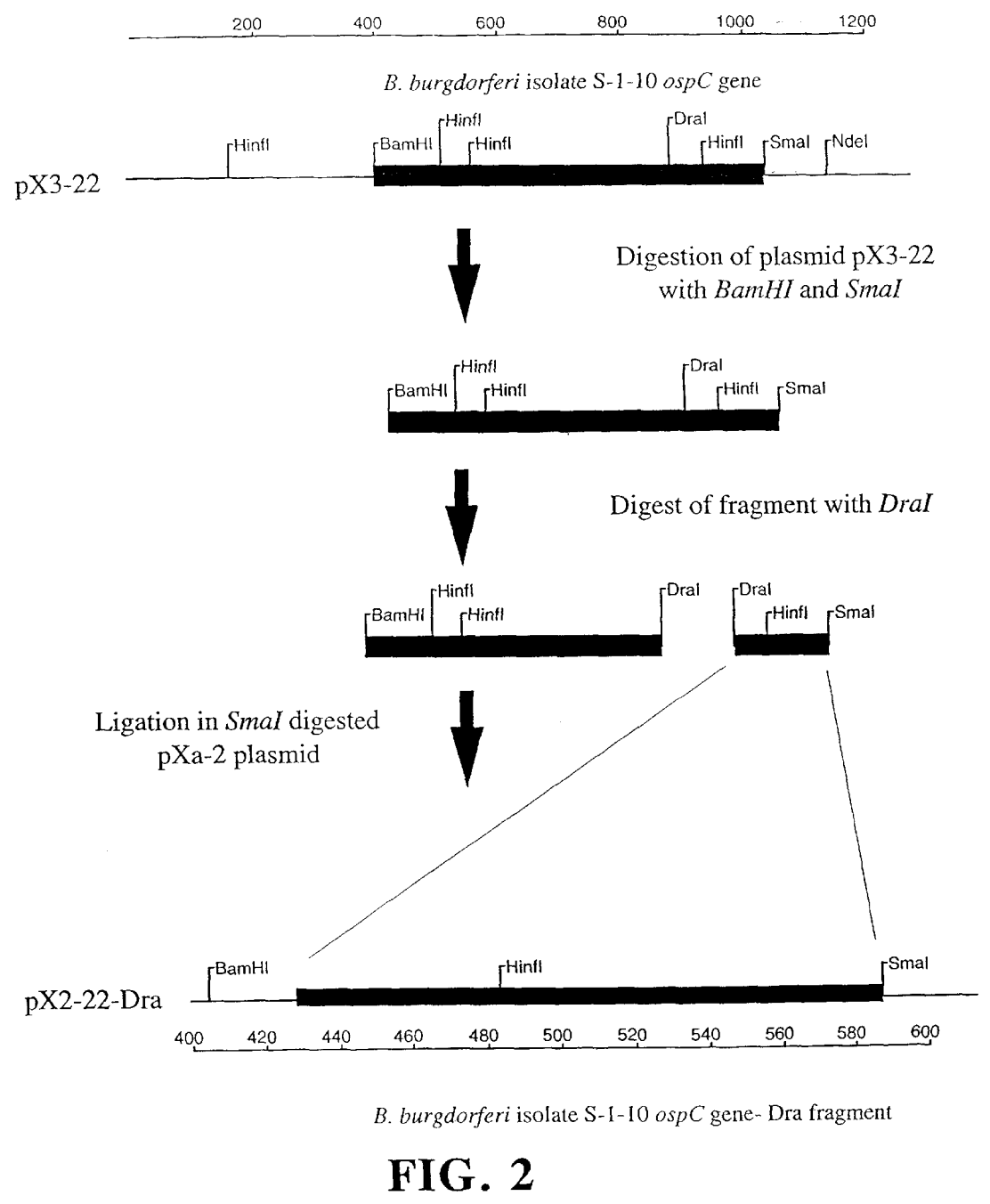

FIG. 2 is a schematic diagram of the steps used to create the plasmid pX2-22-Dra encoding the OspC Dra fragment fusion protein.

Figure 3:
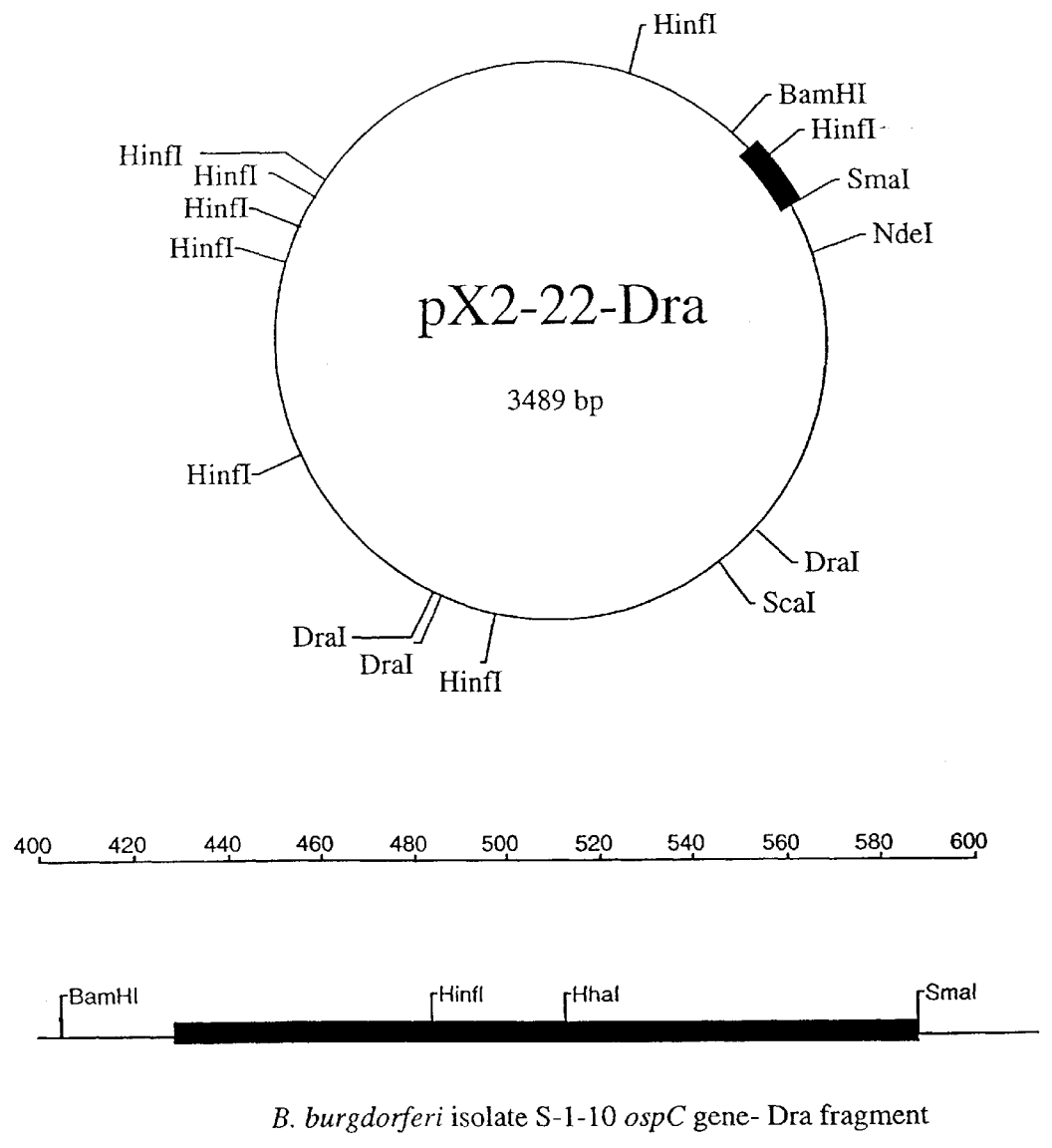

FIG. 3 is a restriction Map of Plasmid pX2-22-Dra. The shaded box represents the area containing the *B.b.* S-1-10 ospC Dra fragment gene.

FIG. 4 is the DNA and encoded amino acid sequence of the Dra fragment fusion protein. The boxed area is the DNA and predicted amino acid sequence unique to the OspC Dra fragment of *B.b.* S-1-10. See also SEQ ID NO:1.

DETAILED DESCRIPTION OF THE INVENTION

The present invention is directed to the discovery and characterization of the epitope(s) of OspC which are responsible for inducing borreliacidal antibodies shortly after infection with *B.b.* This antigenic determinant provides for a superior diagnostic antigen that detects early Lyme disease infection, predicts successful eradication of the organism from the host, and discriminates between individuals with Lyme disease and individuals who have been vaccinated with an OspA Lyme disease vaccine. In addition, the borreliacidal OspC epitope(s) are useful as a vaccine against infection with *B.b.* and the borreliacidal antibodies generated against the OspC epitope are useful as therapy for resolving established *B.b.* infection and disease.

The inventors have discovered anti-OspC borreliacidal antibodies. The discovery of antibodies in Lyme disease sera which specifically kill *B.b.* 50772 (infra.), a tick isolate which does not have the genes to make OspA or OspB, led the inventors to speculate that the surface protein was OspC and that a highly specific borreliacidal antibody response was being generated to this protein.

In an earlier study, Schwan et al. (28) found that when a tick feeds on a human, the ingestion of blood triggers the *B.b.* organisms to downregulate OspA and OspB, and upregulate OspC. The applicants therefore speculated that this likely has something to do with the ability of the spirochete to pass from the tick into the human. The hypothesis was that the spirochete must need OspC to survive in a new host. Therefore, it was hypothesized that if the spirochete shuts down OspA and OspB, which places OspC on its surface, anti-OspC antibodies may be more effective in preventing infection with *B.b.*

If OspC truly induces an early *B.b.* borreliacidal antibody response, then it follows that detection of this highly specific antibody response can be used to detect Lyme disease more accurately and to monitor elimination of the organism after therapy than with other diagnostic assays that do not detect anti-OspC borreliacidal antibodies.

The Dra Fragment

Taking this one step further, the applicants discovered that the borreliacidal epitope(s) are located on a small fragment of the OspC protein. The OspC protein gene has a total length of about 600 base pairs (bp). The DNA encoding the borreliacidal fragment is about 151 bp. The fragment is unique to borrelia. With reference to Example 2, the DNA sequence of the DraI-SmaI ospC gene fragment (OspC Dra fragment) is shown in FIG. 4. The encoded amino acid sequence of this truncated OspC fusion protein is also shown in FIG. 4.

The fragment is called the Dra fragment, primarily because DraI is the restriction enzyme used to cut the DNA sequence at a particular run of bases which represents the enzyme's recognition site. By using the portion of the ospC gene containing borreliacidal epitope(s), specificity and prognostic potential of diagnostic testing is enhanced without significant loss of sensitivity.

The Dra fragment of the OspC protein is also a more viable vaccine component as compared to the full-length OspC protein. By eliminating the rest of the OspC protein, vaccination problems are minimized because the other parts of the protein are not present, thereby limiting vaccination side-effects and making it easier to induce, maintain, and monitor the effective protective antibody response. In addition, the immune response can be easily heightened against only the protective portion of the OspC protein by combining the Dra fragment with an adjuvant such as tetanus toxoid or other vaccine adjuvants which cause the immune response to be heightened. The OspC Dra fragment can also be synthesized de novo using conventional solution- or solid-phase peptide chemistry.

Vaccine Candidate

The use of the borreliacidal antibody test to monitor the levels of anti-OspA borreliacidal antibodies has provided important insight into the efficacy of current OspA Lyme borreliosis vaccines (13,21,23). In fact, borreliacidal antibody tests are now the hallmark for monitoring the ability of OspA Lyme disease vaccines to provide protection. Vaccination of gerbils and laboratory mice with OspC also leads to complete protection against experimental challenge and/or tick-borne infection with homologous B.b. isolates. In addition, unlike vaccination with OspA, vaccination with OspC can also result in clearance of spirochetes and resolution of symptoms even if administered after infection with B.b. Thus, an Osp vaccine would be a valuable addition to efforts to ameliorate the impact of Lyme disease.

As stated earlier, investigators have not previously found evidence that OspC vaccines provide protection by inducing borreliacidal antibodies. Other researchers have not detected anti-OspC borreliacidal antibodies after vaccination despite the ability of OspC vaccination to induce protection. Our results, however, confirm that OspC does indeed induce borreliacidal antibodies and other investigators will quickly realize that they were most likely unable to detect anti-OspC borreliacidal antibodies because they used a B.b. organism for testing that did not express OspC on the surface.

Currently no vaccine uses an isolated borreliacidal epitope(s). The present invention describes the use of the borreliacidal epitope(s) of OspC, as a diagnostic test for, and as a vaccine against Lyme disease.

Pharmaceutical Composition

As a pharmaceutical composition, the present invention includes a pharmaceutically acceptable carrier and a therapeutically effective amount of the OspC Dra polypeptide of this invention. By "therapeutically effective amount," is meant the amount of polypeptide or antibody that, when administered to an animal, elicits an immune response that is effective to prevent or lessen the severity, for some period of time, of B.b. infection.

The administration of the polypeptide or antibody of this invention to the animal may be accomplished by a variety of standard procedures. Preferably, if a polypeptide is used, it will be administered with a pharmaceutically acceptable adjuvant, such as complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve 2 or more administrations of the polypeptide, spread out over several weeks.

The pharmaceutical composition can be used to treat or prevent Lyme disease in various animals, including humans. The pharmaceutical composition may be in a variety of conventional forms, such as tablets, pills, powders, liquids or suspensions, capsules, suppositories, injectable and infusible solutions, all well known to the art. The preferred form depends upon the intended mode of administration and prophylactic application. However, in most applications, the preferred route of administration is parenteral, and most preferably intramuscularly.

The present invention is also directed to a method of treating or preventing B. burgdorferi infection or Lyme disease comprising administering to a patient a therapeutically effective amount of this pharmaceutical composition.

The present invention provides for a kit for diagnosing borrelia infection in mammals, including humans. The kit comprises an isolated polypeptide having an amino acid sequence as shown in residues 145 to 194 of SEQ. ID. NO: 2, disposed in a suitable container therefor, and instructions for use of the kit. Preferably, the isolated polypeptide has an amino acid sequence as shown in SEQ. ID. NO: 2.

EXAMPLES

In order to more fully illustrate the present invention, the following Examples are provided. The Examples, which make reference to the attached figures, are for illustration purposes only to aid in a more complete understanding of the invention. The Examples do not limit the scope of the invention disclosed and claimed herein in any fashion.

Example 1

This example demonstrates the ability of B.b. OspC to induce high levels of borreliacidal antibodies when administered shortly after B.b. infection.

Materials and Methods

Organisms. B.b. sensu stricto isolate 297 (deposited with American Type Culture Collection, 10801 University Blvd., Manassas, Va. 20110 under ATTC Accession Number 53899) was isolated from human spinal fluid. B.b. sensu stricto isolate 50772 (deposited with the American Type Culture Collection on Jul. 30, 1999 according to the terms of the Budapest Treaty), originally isolated from an I. scapularis tick, was obtained from John F. Anderson (Connecticut Agricultural Experiment Station, New Haven, Conn.). The spirochete lacks the OspA/B operon and hence does not express OspA or OspB (25). The original suspensions of spirochetes were serially 10-fold diluted in Barbour-Stoenner-Kelly (BSK) medium capable of supporting growth from a single organism (46). The resultant population of spirochetes was then passaged 10 times in fresh BSK medium at 30° C. or 35° C., dispensed into 200 µl aliquots in 1.5 ml screw-cap tubes (Sarstedt, Newton, N.C.), and stored at −70° C. until used. E. coli JM109 (Promega Corp., Madison, Wis.) was used in all cloning experiments.

Animals. 10 week old female C3H/HeJ mice (Jackson Laboratories, Bar Harbor, Me.) were housed three per cage at ambient temperature. Food and water were available ad libitum.

Sera. Lyme borreliosis sera were obtained from patients at the Gundersen Lutheran Medical Center, La Crosse, Wis. Ten Lyme borreliosis sera samples were from individuals with clinician-documented single or multiple erythema migrans lesions. Two of these sera samples were from patients with dermal skin cultures positive for B.b. Serum from an individual not exposed to B.b. sensu lato was used as a normal serum control. This serum sample was tested by 516 laboratories participating in the national Lyme Proficiency Survey sponsored by the Wisconsin State Laboratory of Hygiene and the College of American Pathologists and was reported as negative for antibodies against B.b. (31).

Western Blotting. Western blotting was performed as previously described (17). Briefly, B.b. 50772 cells were boiled in sample buffer for 5 min and 150 µg of total protein was loaded onto a 0.1% SDS-12% polyacrylamide gel (4% polyacrylamide stacking gel without comb). Protein concentrations were determined with the Bio-Rad protein determination kit following the manufacturer's instructions (Bio-Rad Inc., Richmond, Calif.). Two gels were run simultaneously in an electrophoresis unit (SE600;Hoefer Scientific Instruments, San Francisco, Calif.) at 55 mA for 3 hours with the buffer system of Laemmli (32). After electrophoresis, proteins were transferred to nitrocellulose for 3 hours at 300 mA under conditions described by Towbin et al. (33). The nitrocellulose was cut into strips and blocked with phosphate buffered solution (PBS)-0.3% TWEEN 20 brand detergent for 30 min at 22° C. Strips were incubated for 1 hour at 22° C. with human serum diluted 1:100 and washed 3 times with PBS-0.05% TWEEN 20 brand detergent. Horseradish peroxidase-labeled anti-human IgM or IgG (heavy and light chains; Organon Teknika Cappel, Malvern, Pa.) was added and the strips were incubated for 30 min at 22° C. After incubation, strips were washed and developed (TMB Membrane Peroxidase Substrate System; Kirkegaard & Perry Laboratories, Gaithersburg, Md.).

Cloning and Amplification of the ospC Gene. Plasmid-enriched DNA was isolated from $B.b.$ sensu stricto isolate S-1-10 (13). The DNA was used as a template for the amplification of the ospC gene using the GeneAmp kit (Perkin Elmer Cetus, Norwalk, Conn.) (34). Primers were used at a final concentration of 1.0 $\mu$M in a 1.5 mM concentration of $MgCl_2$. Thermal cycling parameters were 95° C. for 5 minutes followed by 35 cycles of the following: 1) 95° C. for 30 sec, 2) 50° C. for 30 sec, 3) 72° C. for 90 sec. The final extension was done at 72° C. for 7 min to fully extend any truncated DNA strands. The amino-terminal primer C1 (5'-CGTGGATCCATGAAAAAGAATACATTAAGTGCGATA-3') and the carboxy-terminal primer C2 (5'-AATTCCCGGGTTAAGGTTTTTTTGGACTTTCTGC-3') were used for amplification. Underscores indicate regions recognized by the primers. Amplified DNA was purified using GeneClean (Bio101, La Jolla, Calif.). After digestion with SmaI and BamHI (Gibco BRL, Gaithersburg, Md.), purified DNA fragments were ligated into the PinPoint pXa-3 vector (Promega Corp., Madison, Wis.) with T4 DNA ligase (Gibco BRL, Rockville, Md.). The ligation mixture was used to transform competent $E.$ $coli$ JM109. Transformed $E.$ $coli$ were plated onto 2×TY medium containing ampicillin (100 $\mu$g per ml, Sigma Chemical Co., St. Louis, Mo.) and incubated for 24 hours at 37° C. Colonies expressing OspC were detected by Western blot analysis using a streptavidin-horseradish peroxidase conjugate (Gibco BRL) and an early Lyme disease serum containing anti-OspC antibodies.

The DNA sequence of the ospC gene was determined by double-stranded sequencing (TaqTrack, Promega, Madison, Wis.). Analysis and BLAST searches were performed using the GCG software system (GCG, Madison, Wis.). The ospC gene of $B.b.$ sensu stricto S-1-10 was similar (78.5%) to $B.b.$ sensu stricto B31 (35). In addition, the S-1-10 OspC nucleotide sequence differed by 3 bases (98% homology) with $B.b.$ sensu stricto (36).

Purification of Recombinant OspC. $E.$ $coli$ containing the ospC gene were grown in 100 mL of 2×TY broth containing ampicillin for 12 h at 37° C. The culture was diluted 1:10 with 2×TY broth and incubated for an additional 1 h. Isopropyl-B-D-thiogalactopyranoside (final concentration 0.1 mM, Sigma) was added to the culture and incubated for an additional 4 h. The suspension was centrifuged at 10,000×g for 15 min at 4° C., resuspended in purification buffer (50 mM Tris (pH 8.0), 50 mM NaCl, 2 Mm EDTA, 0.1% Triton X-100 brand buffer), and lysed with a sonicator (Model W350; Branson Sonic Power Co., Danbury, Conn.). Sonicated $E.$ $coli$ were centrifuged at 10,000×g for 15 min and the supernatant was passed over a column containing SoftLink resin (Promega, Madison, Wis.) at a rate of 0.5 mL per min at 4° C. The column was then washed with 5 column volumes of purification buffer. OspC was eluted with 5 mM biotin (Sigma) and the recovered fractions were analyzed by SDS-PAGE.

OspC ELISA. Recombinant OspC was diluted to 750 ng/mL in coating buffer (0.015M $Na_2CO_3$, 0.035M $NaHCO_3$, pH 9.6) and 100 $\mu$l amounts were added to individual flat-bottom microtiter wells (Dynatech Laboratories, Chantilly, Va.). Microtiter plates were incubated at 35° C. for 4 hours followed by an overnight incubation at 4° C. After incubation, plates were washed 3 times with phosphate-buffered-saline (PBS, pH 7.2) containing 0.05% TWEEN 20 brand detergent, sealed, and stored at 4° C. Before using, plates were blocked with PBS-0.05% TWEEN 20 detergent containing 1% bovine serum albumin for 30 min at 22° C., washed twice with PBS-0.05% TWEEN 20 brand detergent, and 100 $\mu$l of serial 2-fold dilutions of normal or $Lyme$ $borreliosis$ serum in PBS were added to individual wells. Plates were incubated for 1 hour at 22° C. followed by 3 washes with PBS-0.05% TWEEN 20 brand detergent. 100 microliters of anti-human IgM horseradish peroxidase-conjugated antibody (Organon Teknika Cappel) diluted 1:3000 in PBS-0.05% TWEEN 20 brand detergent were added and plates were incubated at 22° C. for 1 h. After incubation, 100 $\mu$l of o-phenylenediamine phosphate (0.4 mg/mL, Sigma) was added to each well and incubated at 22° C. for 30 min. Reactions were stopped by addition of 100 $\mu$l of 1N $H_2SO_4$ and absorbances at 490 nm (Model EL307, Bio-Tek Instruments, Inc., Winooski, Vt.) were immediately determined. An OD value>0.200 above the normal serum control was considered positive.

Detection of Borreliacidal Antibodies. The flow cytometric borreliacidal antibody test was performed according to Callister et al. (29,30). Briefly, a frozen 200 $\mu$l aliquot of $B.b.$ isolate 50772 or 297 was thawed, inoculated into 6 mL of fresh BSK medium, and cultures were incubated for 72 hours at 35° C. After incubation, the concentration of spirochetes was determined using a Petroff-Hausser counting chamber and diluted in fresh BSK medium to a concentration of $10^6$ organisms per milliliter. Serum samples were diluted 1:20 in fresh BSK medium and sterilized by passage through a 0.2-$\mu$m microfuge filter (Costar, Cambridge, Mass.). A 100 $\mu$l aliquot was transferred to a 1.5 mL screw-cap microfuge tube (Sarstedt) and the diluted serum was heat-inactivated at 56° C. for 10 min. Following heat-inactivation, a 100 $\mu$l aliquot of $B.b.$ 50772 and 15 $\mu$l of sterile guinea pig serum (200, 50% hemolytic complement units per ml; Sigma) was added to the diluted sera. After gentle agitation, the assay suspensions were incubated for 16–24 hours at 35° C.

Following incubation, 100 $\mu$l of the assay suspensions were diluted 1:5 with PBS (0.01 mol/L, pH 7.2) containing acridine orange (final concentration, 5.4×$10^9$ mol/L). Borreliacidal antibodies were detected with a FACScan single-laser flow cytometer (Becton-Dickinson Immunocytometry Systems, San Jose, Calif.). Events were acquired for 1 to 2 minutes with the flow rate set at low (12 $\mu$l/min) and analyzed with FACScan Lysys II research software. Side scatter and fluorescence intensity parameters were used to distinguish $B.b.$ from BSK and complement particles. Spirochetes were gated during data acquisition and fluorescence signals were logarithmically amplified and converted to a linear scale. A $\geq$13% increase in fluorescence intensity compared to normal serum controls was considered positive (30). All assays were performed in duplicate or triplicate.

Vaccination of Mice and Recovery of Anti-OspC Sera. Mice were vaccinated intramuscularly with 75 μg of purified OspC in 100 μl of Freund's complete adjuvant (Sigma). Subsequently, mice were boosted with 75 μg-amounts of OspC in 100 μl of Freund's incomplete adjuvant (Sigma) at 2 and 4 weeks after the primary vaccination. Two weeks after the second booster, blood was collected by intracardiac puncture. Blood was allowed to clot and serum was separated by centrifugation at 3500 rpm for 5 min. Serum was removed and stored in 50 μl amounts at −70° C. until used.

Flow Cytometric Immunofluorescence Assay. Mouse serum samples containing anti-OspC antibodies were serially diluted in BSK medium (1:20 to 1:40960). 100 microliters of BSK medium containing $10^5$ live *B.b.* 297 or 50772 organisms were added to each dilution. Suspensions were gently vortexed and incubated at 35° C. for 30 min. After incubation, 10 μl of fluorescein isothiocyanate (FITC)-conjugated goat anti-mouse IgG (ICN/Cappel, Aurora, Ohio) antibodies diluted 1:20 in sterile PBS (pH 7.2) were added to each assay. Assays were gently vortexed and incubated at 35° C. for an additional 30 min. After incubation, 100 μl aliquots of each suspension were combined with 400 μl of 0.22 μm filter-sterilized PBS. These suspensions were then analyzed by using a FACScan flow cytometer.

Neutralization of Borreliacidal Activity. Borreliacidal activity of serum samples after removal of IgM or IgG antibodies was determined as previously described (17). Briefly, 125 μl of dialyzed goat anti-human IgM or IgG (heavy and light chain; Kallestad Diagnostics, Chaska, Minn.) was added to 25 μl of normal or *Lyme borreliosis* serum and the mixture was incubated for 2 hours at 37° C. After centrifugation at 5000×g for 10 min (Surespin; Helena Laboratories, Beaumont, Tex.), the supernatant was diluted 2-fold with fresh BSK medium, sterilized by passage through a 0.2-μm microfuge filter (Costar), and assayed for borreliacidal activity. The borreliacidal activity of normal and *Lyme borreliosis* sera without treatment with anti-IgM or anti-IgG was determined after adding 125 μl of PBS (pH 7.2).

Adsorption of *Lyme Borreliosis* Sera with OspC. Adsorption of anti-OspC antibodies from *Lyme borreliosis* sera was done using a modification of a previously described procedure (17). TetraLink Tetrameric Avidin Resin (Promega) was washed with PBS and a 1 mL volume was loaded into a column. Three micrograms of dialyzed biotinylated OspC in a 1 mL volume was passed over the column and absorbance (OD) at 280 nm was monitored to confirm binding of OspC to the column. A 1 mL sample of each of 10 human *Lyme borreliosis* sera diluted tenfold with PBS (pH 7.2) was then passed over the column 10 to 15 times at 4° C. to remove anti-OspC antibodies. Removal of anti-OspC antibodies was confirmed by Western blotting.

This study showed that vaccination of mice with OspC induced high concentrations of anti-OspC borreliacidal antibodies, and led to increased efforts (in the following examples) to evaluate the ability of OspC to provide protection against infection with *B.b.*, because it provides a plausible immune mechanism explaining the ability of an OspC vaccination to protect against or cure Lyme disease. Moreover, it was discovered that large concentrations of anti-OspC borreliacidal antibodies can easily be detected in serum from patients throughout the U.S. when only a single organism, *B.b.* 50772, is used as the test antigen, which also indicates that the anti-OspC borreliacidal epitope(s) may be conserved. Thus, the OspC heterogeneity will not hinder efforts to develop a comprehensive OspC vaccine.

These findings are in direct contrast to other published observations. In previous reports, detection was dependent on the presence of high levels of OspC on the surface of *B.b.* These anti-OspC borreliacidal antibodies were detected only when *B.b.* isolate 50772, which expresses high levels of OspC on the surface, was used.

Example 2

This example demonstrates that the borreliacidal epitopes of OspC are located within the Dra fragment region.

Step a: Isolation of Plasmids, Cloning, and Amplification of the ospC Gene. Plasmid-enriched DNA was isolated from *B.b.* sensu stricto isolate S-1-10 using standard techniques (13). The DNA was then used as a template for the amplification of the ospC gene by the GeneAmp protocol (Perkin Elmer Cetus, Norwalk, Conn.) using the polymerase chain reaction (34). Primers were used at a final concentration of 1.0 μm with a $MgCl_2$ concentration of 1.5 mM. Thermal cycling parameters were 95° C. for 5 min followed by 35 cycles of the following: 1) 95° C. for 30 sec, 2) 50° C. for 30 sec, 3) 72° C. for 90 sec. The final extension was done at 72° C. for 7 min to fully extend any truncated DNA strands. The amino-terminal primer C1 5'-CGTGGATCCATGAAAAAGAATACATTAAGTGCGATA-3' and the carboxy-terminal primer C2 5'-AATTCCCGGGTTAAGGTTTTTTTGGACTTTCTGC-3' were used for amplification. The amplified DNA was purified using GeneClean (Bio101, La Jolla, Calif.). After digestion with SmaI and BamHI (Bethesda Research Laboratories, Gaithersburg, Md.), the purified DNA fragments were ligated into the PinPoint pXa-3 vector (Promega Corp., Madison, Wis.). The insert and plasmid were ligated with T4 DNA ligase (Bethesda Research Laboratories) and the ligation mixture was used to transform competent *E. coli JM*109. Subsequently, organisms were plated onto 2×tryptone yeast (TY) medium containing ampicillin (100 μg/ml, Sigma Chemical Co., St. Louis, Mo.) and incubated for 24 hour at 37° C. Colonies expressing the OspC fusion protein were detected by Western blot analysis using a streptavidin-alkaline phosphatase conjugate (Bethesda Research Laboratories) and an early Lyme disease serum containing anti-OspC antibodies. This plasmid was given the designation pX3-22 and is illustrated in FIG. 1.

Step b: Creation of the ospC Gene Truncation. In order to make a carboxy terminal fragment of the OspC protein, plasmid pX3-22 was digested with restriction enzymes BamHI and SmaI (Gibco). The ~0.6 kb BamHI-SmaI fragment containing the ospC gene was then digested with restriction enzyme DraI (Gibco) as illustrated in FIG. 2. This digestion resulted in a ~0.4 kb BamHI-DraI fragment which codes for the amino-terminal end of the OspC protein and a ~0.2 kb DraI-SmaI fragment which codes for the carboxy-terminal end. This DraI-SmaI fragment was then ligated with SmaI digested PinPoint vector pXa-2 (Promega Corporation, Madison, Wis.) to preserve the proper reading frame of the resulting truncated protein. The ligation mixture was used to transform competent *E. coli JM*109. Restriction digests were performed to identify a clone with the proper orientation of the ospC gene fragment insertion. This plasmid was designated pX2-22-Dra and is illustrated in FIG. 3.

Step c: Molecular Analysis of the ospC Gene Fragment. The DNA sequence of the pX2-22-Dra was determined by double-stranded sequencing. Primer C2 (See step a of Example 2), constructed for amplification, and the PinPoint Sequencing Primer (Promega) were used. The sequence of the DraI-SmaI ospC gene fragment (OspC Dra fragment) is shown in FIG. 4. The predicted amino acid sequence of this truncated OspC fusion protein is also shown in FIG. 4.

Step d: Purification of Dra Fragment OspC. Transformed *E. coli* organisms containing either pX3-22 and pX2-22-Dra were grown in 100 ml of 2×TY broth containing ampicillin for 12 hours at 37° C. The culture was diluted 1:10 with 2×TY broth and incubated for an additional 1 hour. Isopropyl-β-D-thiogalactopyranoside (final concentration 0.1 mM, Sigma) was added to the culture and incubated for an additional 4 hours. The suspension of bacteria was then centrifuged (10,000×g for 15 min at 4° C.), resuspended in purification buffer (50 mM Tris (pH 8.0) 50 mM NaCl, 2 mM EDTA, 0.1% "TRITON X-100" brand buffer), and lysed by 5×30 sec pulses with a sonicator (Model W350; Branson Sonic Power Co., Danbury, Conn.). The sonicated *E. coli* organisms were centrifuged at 10,000×g for 15 min to remove insoluble material, and the supernatant was passed over a column of SoftLink resin (Promega) at a rate of 0.5 ml per min at 4° C. The column was then washed with 5 column volumes of purification buffer. Column-bound OspC Dra fragment fusion protein was eluted using purification buffer containing 5 mM biotin (Sigma). Fractions were analyzed by sodium dodecyl sulfate-polyacrylamide gel electrophoresis.

Step e: Adsorption of *Lyme Borreliosis* Sera with Whole and Dra Fragment OspC. Adsorption of anti-OspC or Dra fragment antibodies from *Lyme borreliosis* sera was done using a modification of a previously described procedure (17). TetraLink Tetrameric Avidin Resin (Promega) was washed with PBS and a 1 ml volume was loaded into a column. 3 micrograms of dialyzed biotinylated whole OspC (fusion protein from pX3-22) or Dra fragment OspC (fusion protein from pX2-22-Dra) in a 1 ml volume was then passed over the column and absorbance at 280 nm was monitored to confirm binding of protein to the column. A 1 ml sample of each sera diluted tenfold with PBS (pH 7.2) was then passed over the column 10 to 15 times to remove anti-OspC or anti-Dra fragment antibodies.

Using the materials and methods of Examples 1 and 2, we initially tested 7 early Lyme disease sera samples which contained high titers of anti-OspC borreliacidal antibodies and confirmed that the borreliacidal antibodies were against a specific region of the OspC protein within the Dra fragment described herein.

OspC or Dra fragment fusion proteins were bound to agarose beads and separate immuno-affinity columns were prepared. Lyme disease sera were passed over the columns to remove anti-OspC or anti-Dra fragment antibodies by adsorption to the OspC or Dra fragment fusion proteins, respectively. Borreliacidal activity against *B.b.* 50772 was determined before and after removal of the antibodies. Removal of anti-OspC and anti-Dra fragment antibodies from the early Lyme disease sera caused almost complete abrogation of the borreliacidal activity as illustrated in Table 1.

TABLE 1

Borreliacidal activity of early Lyme disease sera after removal of antibodies against whole OspC or Dra fragment.

| Patient Number | Borreliacidal activity[a] before and (after) removal of OspC antibodies | Borreliacidal activity[a] before and (after) removal of Dra antibodies |
|---|---|---|
| 1 | 10240 (20) | 20480 (80) |
| 2 | 40960 (20) | 40960 (20) |
| 3 | 10240 (40) | 20480 (40) |
| 4 | 640 (20) | 1280 (20) |
| 5 | 2560 (20) | 5120 (20) |
| 6 | 1280 (40) | 5120 (20) |
| 7 | 10240 (320) | 20480 (1280) |

[a]Reciprocal dilution of serum titer

Table 1 shows the borreliacidal Antibody Titer Of early Lyme sera after removal of antibodies against whole OspC fusion protein or OspC Dra fragment. Referring to Table 1, it can be seen that the borreliacidal antibodies were against the specific region of the OspC protein located within the Dra fragment. These results demonstrate that anti-OspC borreliacidal antibodies are almost completely induced by epitope(s) located within the Dra fragment region of OspC.

Example 3

This example demonstrates that anti-OspC antibodies which are specific to the Dra fragment region of OspC can be detected by ELISA.

Dra Fragment ELISA. Purified OspC Dra fragment was diluted to 750 ng/ml in coating buffer (0.015M $Na_2CO_3$, 0.035M $NaHCO_3$, pH 9.6) and added to flat-bottom N-oxysuccinimide surface amino binding microtiter wells. The ELISA plates were incubated at 35° C. for 4 hours followed by an overnight incubation at 4° C. After incubation, plates were washed 3 times with PBS containing 0.05% TWEEN 20 brand detergent, sealed, and stored at 4° C. Before using, plates were blocked with PBS-0.05% TWEEN 20 brand detergent containing 1% bovine serum albumin for 30 min at ambient temperature. Plates were washed twice with PBS-0.05 % TWEEN 20 brand detergent and 100 μl of serial 2-fold dilutions of serum in PBS was added to the individual microtiter wells. Plates were incubated for 1 hour at 22° C. followed by 3 washes with PBS-0.05% TWEEN 20 brand detergent. Anti-human IgM or IgG horseradish peroxidase-conjugated antibody (Organon Teknika Cappel, Malvern, Pa.) was diluted 1:3000 or 1:5000 in PBS-0.05% TWEEN 20 brand detergent. Aliquots (100 μl) of the conjugate were added to the wells and incubated at 22° C. for 1 hour. Subsequently, 100 μl of o-phenylenediamine phosphate (Sigma) was added and the plates were incubated at 22° C. for 30 min. Reactions were stopped by adding 100 μl of 1N $H_2SO_4$ and absorbances at 490 nm were determined.

It was determined whether the anti-Dra fragment antibodies present in the 7 early Lyme disease sera samples could be easily detected by using a Dra fragment IgM or IgG ELISA. Dra fragment ELISA plates were prepared and used to measure the amount of Dra-specific antibody detected when the sera was diluted 1:200 with PBS (pH 7.2) containing 0.5% TWEEN 20 brand detergent. This is a dilution commonly used by diagnostic laboratories when performing ELISA assays. Significant levels of IgM anti-Dra fragment antibodies were detectable in all 7 early Lyme disease sera samples as illustrated in Table 2. The IgG ELISA also detected anti-Dra fragment antibodies in 3 (42%) of the 7 early sera samples. Table 2 illustrates the OspC (whole protein) and Dra fragment IgM ELISA reactivity using early Lyme disease sera (n=7) containing anti-OspC and anti-Dra borreliacidal antibodies. Table 2 shows that a Dra-fragment ELISA could detect anti-Dra fragment antibodies in the early Lyme disease sera at a 0.200 absorbance and a 1:200 dilution.

TABLE 2

Dra fragment ELISA[a] reactivity using early Lyme disease sera (n = 7) containing anti-Dra borreliacidal antibodies.

| Number (%) of sera IgM reactive at: | | | Number (%) of sera IgG reactive at: | | |
|---|---|---|---|---|---|
| ≧0.1 | ≧0.2 | ≧0.3 | ≧0.1 | ≧0.2 | ≧0.3 |
| 7(100) | 7(100) | 7(100) | 3(43) | 0 | 0 |

[a]Sera diluted 1:200 in phosphate buffered saline (pH 7.2) containing 0.05% TWEEN 20 brand detergent. Reactivity determined by absorbance of 490 nm.

Example 4

This example was designed to demonstrate specificity of a *B.b.* OspC ELISA and a Dra fragment ELISA for detecting Lyme disease.

It was determined whether the Dra fragment ELISA was more specific than the OspC ELISA by examining normal sera and sera from patients with EBV and CMV infections. Also tested were sera samples containing rheumatoid factor and sera samples from patients with syphilis because these types of sera are also known to react strongly with conventional Lyme disease tests. In addition, sera samples from individuals previously vaccinated with an OspA Lyme disease vaccine were tested. Both ELISAs were not affected by previous vaccination against Lyme disease. Similar small numbers of the normal serum samples, the sera containing the rheumatoid factor and the syphilitic sera were positive using the IgM OspC or Dra fragment ELISAs. However, the OspC ELISA was often falsely positive using sera from patients with other illnesses, including EBV and CMV, primarily when testing for IgM. This is not surprising since IgM antibodies are present in high concentrations during early Lyme disease. IgG antibodies do not commonly appear until later stages of the illness. In contrast, the IgM Dra fragment ELISA was significantly less reactive using sera from patients with CMV and EBV. Reference is made to Table 3 below. Thus, the Dra fragment ELISA was significantly more specific than the ELISA containing the whole OspC protein.

Table 3 shows the IgM OspC (whole protein) and Dra fragment ELISA versus Lyme Disease cross-reactive sera (serum dilution 1:200). Referring to Table 3, the Dra fragment ELISA was significantly more specific than the OspC ELISA.

TABLE 3

Number (%) of potentially cross-reactive sera with OspC and Dra fragment IgM ELISA reactivity[a]

| Sera (Number Tested) | Number (%) of positive results using OspC ELISA | | | Number (%) of positive results using Dra ELISA | | |
|---|---|---|---|---|---|---|
| | ≧0.100 | ≧0.200 | ≧0.300 | ≧0.100 | ≧0.200 | ≧0.300 |
| Endemic Normal (28) | 1 (3.6) | 0 | 0 | 0 | 0 | 0 |
| CMV (39) | 11 (28.2) | 7 (17.9) | 3 (7.6) | 3 (7.6) | 0 | 0 |
| EBV (47) | 12 (25.5) | 3 (6.4) | 3 (6.4) | 1 (2.1) | 0 | 0 |
| Syphilis (25) | 3 (12.0) | 2 (8.0) | 0 | 4 (16.0) | 2 (8.0) | 1 (4.0) |
| Rheumatoid factor (15) | 2 (13.3) | 2 (13.3) | 2 (13.3) | 2 (13.3) | 2 (13.3) | 2 (13.3) |
| Total (154) | 29 (18.8) | 14 (17.0) | 8 (5.2) | 10 (6.5) | 8 (5.2) | 3 (1.9) |

[a]Sera diluted 1:200 in phosphate buffered saline (pH 7.2) containing 0.05% TWEEN 20 brand detergent. Absorbance determined at 490 nm.

Example 5

This example was designed to show that the OspC and Dra fragment ELISA had similar sensitivities. The sensitivity of the Dra fragment ELISA was compared to the OspC ELISA by examining 20 sera samples from patients with culture-defined Lyme disease. These sera also contained varying levels of anti-OspC borreliacidal antibodies. The OspC and Dra fragment ELISAs had similar sensitivity. The OspC and Dra fragment ELISAs detected IgM antibodies (absorbance ≧0.200) in 12 (60%) and 10 (50%) of the 20 early Lyme disease sera, respectively as illustrated in Table 4.

TABLE 4

Detection of OspC or Dra fragment antibodies by IgM ELISA[a] in 20 early Lyme disease sera samples containing anti-*B. burgdorferi* 50772 borreliacidal antibodies.

| ELISA | Number (%) of sera IgM reactive at: | |
|---|---|---|
| | >0.100 | >0.200 |
| OspC | 15 (75) | 12 (60) |
| Dra fragment | 12 (60) | 10 (50) |

[a]Sera diluted 1:200 in phosphate buffered saline (pH 7.2) containing 0.05% TWEEN 20 brand detergent. Absorbance values were determined at 490 nm.

In addition, the ability to detect anti-OspC or anti-Dra fragment antibodies correlated closely with the anti-*B.b.* borreliacidal activity. With few exceptions, high concentrations of anti-OspC or anti-Dra fragments IgM antibodies were detected in early Lyme disease sera which also contained high concentrations of borreliacidal antibodies. When borreliacidal activity was low, both ELISAs were most often negative. This was not unexpected since the borreliacidal antibody test has been shown to be approximately 3 times more sensitive than a commercial ELISA (30).

Example 6

We are currently working to improve the sensitivity of the Dra fragment ELISA by lowering the dilutions of serum tested. This should be easily possible because of the highly specific nature of the Dra fragment antibody response. We anticipate that refinements of the Dra fragment ELISA test procedures (e.g., serum dilution, concentration of antigen/well) will significantly increase the sensitivity to levels more closely related to anti-*B.b.* 50772 borreliacidal antibody detection sensitivity.

Example 7

This example confirms the prognostic ability of the Dra fragment ELISA. Multiple sera samples from 2 early Lyme disease patients were tested using the Dra fragment ELISA. Serum samples were collected before, during and after treatment with antimicrobial agents. Anti-50772 borreliacidal activity was monitored with the Dra fragment ELISA. In patient 1, anti-OspC antibodies were detectable 5 days after infection and 6 and 11 days after antibiotic treatment was initiated. Anti-50772 borreliacidal antibody and anti-Dra fragment antibodies were detectable 5 days after infection and 6 days after treatment, but were no longer detectable after 11 days. Similarly, anti-OspC antibodies were detectable 7 days after infection and 10 and 24 days after antibiotic treatment in the serum from patient 2. However, borreliacidal antibodies and anti-Dra fragment antibodies were only detectable before antibiotic treatment. These results demonstrate the ability of the Dra fragment ELISA to correlate with infection with *B.b.* Thus, the Dra fragment ELISA is also useful as a "test of cure."

Example 8

The ability of OspC to induce borreliacidal antibodies has enabled the identification of the epitope(s) responsible for inducing the activity. Because protection after vaccination with OspA is dependent on the induction and maintenance of high levels of anti-OspA borreliacidal antibodies, protection or clearance of *B.b.* from infected individuals will also be dependent on induction of anti-OspC borreliacidal antibodies. Because the anti-OspC borreliacidal antibodies can be removed from early Lyme disease sera by adsorption to the Dra fragment, vaccination with the Dra fragment should also induce borreliacidal antibodies. Mice vaccinated with recombinant OspC do, in fact, produce borreliacidal antibodies.

Utilizing the methods of Example 1, mice were vaccinated with *B.b.* 50772 and the level of borreliacidal antibodies was determined at various time intervals after vaccination. Borreliacidal activity was detectable 14 days after the initial vaccination and peaked after 56 days as shown in Table 5.

TABLE 5

Development of anti-*B. burgdorferi* 50772 borreliacidal antibodies in mice after vaccination with *B. burgdorferi* 50772 organisms.

| Days after primary vaccination[a] | Borreliacidal activity against B burgdorferi 50772 | |
|---|---|---|
| | Mouse 1 | Mouse 2 |
| 14 | 20[b] | 20 |
| 28 | 320 | 320 |
| 42 | 160 | 160 |
| 56 | 2560 | 640 |
| 112 | 1280 | 320 |

[a]Mice were vaccinated on Day 0 and given four booster vaccinations at two week intervals.
[b]Reciprocal of highest serum dilution with significant borreliacidal activity.

In a related experiment, anti-Dra fragment antibodies were removed by adsorption to anti-Dra fragment fusion protein. The borreliacidal antibody levels were then measured before and after adsorption and removal of anti-Dra fragment antibodies. Borreliacidal activity decreased from 1:2560 to 1:640 after removing anti-Dra fragment antibodies. Thus, vaccination with the Dra fragment will induce protective borreliacidal antibodies.

Example 9

The example is designed to show that the Dra fragment is the better vaccine candidate than the entire OspC protein. Animals are vaccinated with OspC and serum with high levels of borreliacidal activity are collected. The serum is split and the borreliacidal activity from 1 sample is eliminated by removal of anti-Dra fragment antibodies. The animals which do or do not contain borreliacidal antibodies (anti-Dra fragment) to separate groups of recipient animals are then passively administered before challenging them with *B.b.* and at various intervals after infection. The serum containing anti-Dra fragment borreliacidal antibodies will protect against and eliminate organisms and clinical symptoms after infection. In contrast, we expect the anti-OspC serum without borreliacidal antibodies to be ineffective at preventing or curing infection. Thus, there is definitive evidence of the utility of the Dra fragment as an important Lyme disease vaccine component.

Example 10

Lyme disease also causes considerable morbidity and some mortality among dogs and cats. There are similarities between the disease in humans and dogs including migration of the spirochetes to joints and development of Lyme arthritis (45). Interestingly, Straubinger et al. (27) recently reported that, unlike humans, naturally-infected dogs do not produce borreliacidal antibodies.

We, however, recently demonstrated that naturally infected dogs do indeed develop high concentrations of borreliacidal antibodies. We naturally infected 15 12–24 week old pathogen-free beagles by attaching 10 female and 6 male *Ixodus scapularis* ticks to the animals and allowing them to feed to repletion. Approximately 44% of the ticks were infected with *B.b.* High concentrations of anti-*B.b.* 50772 borreliacidal antibodies were detectable in 8 (53%) of 15 dogs 1 week after the tick were attached. Reference is made to Table 6.

TABLE 6

Detection of borreliacidal antibodies against *B. burgdorferi* 50772 in canine sera after tick challenge[a].

| Weeks post-challenge | No. of sera with cidal antibodies[b]/Total (%) | Mean borreliacidal activity[c] |
|---|---|---|
| Prechallenge | 0/14 (0) | NRD[d] |
| 1 | 8/15 (53) | 518 |
| 2 | 12/14 (86) | 402 |
| 3 | 13/15 (87) | 558 |
| 4 | 13/15 (87) | 1645 |
| 5 | 13/15 (87) | 2074 |
| 6 | 13/15 (87) | 3700 |
| 7 | 13/15 (87) | 3814 |
| 8 | 12/14 (86) | 2552 |
| 9 | 12/13 (92) | 2407 |

[a]Ten female and six male *Ixodes scapularis* ticks allowed to feed to repletion (forty-four percent of ticks were infected with *B. burgdorferi*. Probability of last challenged dog receiving at least one infected tick was 99.4%. All ticks were collected from an endemic Lyme disease focus near Ettrick, WI).
[b]Significant borreliacidal activity at a serum dilution ≧ 1:20.
[c]Reciprocal dilution of average borreliacidal antibody titer.
[d]NRD, no response detected.

From 2 to 9 weeks after infection, ≧86% of the dogs had high concentrations of borreliacidal antibodies in their serum. In addition, 83% of the infected dogs developed clinical signs and symptoms (lameness) associated with Lyme disease and *B.b.* organisms were recovered from the skin and joints of >90% of the animals. We also removed anti-OspC and anti-Dra fragment antibodies from 3 dog sera with high titers of anti-*B.b.* 50772 borreliacidal antibodies. Removal of these antibodies resulted in almost complete abrogation of the borreliacidal activity. These findings are almost identical to our results using human sera. Thus, it is likely that the OspC Dra fragment will be useful for companion animals in the same ways as described above for humans.

It is understood that the invention is not confined to the particular construction and arrangement of parts herein illustrated and described, but embraces such modified forms thereof as come within the scope of the claims following the Bibliography.

Bibliography

1. Centers for Disease Control and Prevention. (1996) *Morbid. Mortal. Weekly Report* 45:481–484
2. Centers for Disease Control and Prevention. (1996) *Morbid. Mortal. Weekly Report* 46:531–535
3. Steere A. C. et al. (1983) *Ann. Intern. Med.* 99:76–82
4. Pachner A. R. (1985) *Neurology* 35:47–53
5. Steere A. C. (1980) Ann. Intern. Med. 93:8–16
6. Agger W. A. (1991) *Medicine* 70:83–90
7. Johnson R. C. et al. (1986) *Infect. Immun.* 53:713–4
8. Schmitz J. L. et al. (1990) *Infect. Immun.* 58:144–8
9. Schmitz J. L. et al. (1991) *Infect. Immun.* 59:1916–21
10. Lovrich S. D. et al. (1993) *Infect. Immun.* 61:4367–74
11. Lovrich S. D. et al. (1994) *J. Infect. Dis.* 170:115–21
12. Fikrig E. et al. (1992) *Infect. Immun.* 60:657–61
13. Lovrich S. D. et al. (1995) *Infect. Immun.* 63:2113–9
14. Probert W. S. et al. (1994) *Infect. Immun.* 62:1920–6
15. Probert W. S. et al. (1997) *J. Infect. Dis.* 175:400–5
16. Gilmore R. D. et al. (1996) *Infect. Immun.* 64:2234–9
17. Callister S. M. et al. (1993) *J. Infect. Dis.* 167:158–64
18. Fikrig E. et al. (1994) *J. Infect. Dis.* 169:568–74
19. Sadziene A. et al. (1993) *J. Infect. Dis.* 167:165–72
20. Sambri V. et al. (1993) *FEMS Immunol. Med. Microbiol.* 7:67–72
21. Johnson B. J. B. et al. (1995) *Vaccine* 13:1086–94
22. Ma J. et al. (1995) *Infect. Immun.* 63:2221–7
23. Padilla M. L. et al. (1996) *J. Infect. Dis.* 174:739–46
24. Sadziene A. et al. (1994) *Infect. Immun.* 62:2037–45
25. Zhang Y. Q. et al. (1997) *J. Clin. Microbiol.* 35:233–8
26. Schutzer S. E. et al. (1997) *N. Engl. J. Med.* 337:794–5
27. Straubinger R. K. et al. (1995) *J. Clin. Microbiol.* 33:2745–51
28. Schwan T. G. et al. (1995) *Proc. Natl. Acad. Sci. USA* 92:2909–13
29. Callister S. M. et al.(1994) *J. Clin. Microbiol.* 29:1773–6
30. Callister S. M. et al.(1996) *Clin. Diagn. Lab. Immunol.* 3:399–402
31. Bakken L. L. et al. (1997) *J. Clin. Microbiol.* 35:537–43
32. Laemmli I. K. (1970) *Nature* 227:680–5
33. Towbin H. et al. (1979) *Proc. Natl. Acad. Sci. USA* 76:4350–4
34. Leck K et al. (1987) *Current Protocols in Molecular Biology.* New York: John Wiley and Sons
35. Padula S. J. (1993) *Infect. Immun.* 61:5097–105
36. Thiesen M. et al. (1995) *J. Bacteriol.* 177:3036–44
37. Schell R et al. (1997) *J. Spiro. Tick-borne Dis.* 4:4–6
38. Rauer S. et al. (1998) *J. Clin. Microb.* 36:857–861
39. Magnarelli L. et al. (1996) *J. Clin. Microb.* 34:237–240
40. Fung B. et al. (1994) *Infect. Immun.* 62:3213–3221
41. Gerber M. et al. (1995) *J. Infect. Dis.* 171:724–727
42. Padula S. et al. (1994) *J. Clin. Microb.* 32:1733–1738
43. Creson J. et al. (1996) *Clin. & Diag. Lab. Immun.* 3/2:184–190
44. Zhong W. et al. (1999) *Eur. J. Immunol.* 29:946–947
45. Appel M et al. (1993) *J. Inf. Dis.* 67:651–654
46. Callister S et al. (1990) *J. Clin. Microbiol.* 28:363–5

---

What is claimed is:

1. An isolated, immunogenic polypeptide fragment of outer surface protein C (OspC) of *Borrelia burgdorferi* consisting essentially of an epitope of OspC having an amino acid sequence as shown in residues 145 to 194 of SEQ. ID. NO: 2.

2. An isolated polypeptide having an amino acid sequence as shown in SEQ. ID. NO: 2.

3. The isolated polypeptide of claim 2, further having an amino acid sequence as shown in residues 145 to 194 of SEQ ID NO: 2.

4. A pharmaceutical composition to vaccinate against and to treat borrelia infection in mammals, including humans, the composition comprising an amount of an isolated polypeptide consisting essentially of an amino acid sequence as shown in SEQ. ID. NO: 2, the amount being effective to vaccinate against or to treat borrelia infection in mammals.

5. The pharmaceutical composition of claim 4, further comprising a pharmaceutically suitable carrier.

6. The pharmaceutical composition of claim 4, wherein the isolated polypeptide consists essentially of an amino acid sequence as shown in residues 145 to 194 of SEQ. ID. NO: 2.

7. The pharmaceutical composition of claim 6, further comprising a pharmaceutically suitable carrier.

8. The pharmaceutical composition of claim 4, further comprising an adjuvant.

9. The pharmaceutical composition of claim 6, further comprising an adjuvant.

10. A kit for diagnosing borrelia infection in mammals, including humans, the kit comprising an isolated polypeptide having an amino acid sequence as shown in SEQ. ID. NO: 2, disposed in a suitable container therefor, and instructions for use of the kit.

11. The kit of claim 10, wherein the isolated polypeptide has an amino acid sequence as shown in residues 145 to 194 of SEQ. ID. NO: 2.

* * * * *